(12) United States Patent
Knott et al.

(10) Patent No.: US 9,107,968 B2
(45) Date of Patent: Aug. 18, 2015

(54) APPARATUS AND METHOD OF RADIATION-BASED STERILIZATION OF CONTAINER CLOSURES

(71) Applicant: Krones AG, Neutraubling (DE)

(72) Inventors: Josef Knott, Schierling (DE); Guenter Frankenberger, Koefering (DE); Tino Sickert, Dresden (DE)

(73) Assignee: KRONES, AG, Neutraubling (DE)

( * ) Notice: Subject to any disclaimer, the term of this patent is extended or adjusted under 35 U.S.C. 154(b) by 264 days.

(21) Appl. No.: 13/859,320

(22) Filed: Apr. 9, 2013

(65) Prior Publication Data

US 2013/0272920 A1    Oct. 17, 2013

(30) Foreign Application Priority Data

Apr. 11, 2012 (DE) .......................... 10 2012 103 116

(51) Int. Cl.
| | |
|---|---|
| *A61L 2/00* | (2006.01) |
| *B01J 19/08* | (2006.01) |
| *G01N 23/00* | (2006.01) |
| *A61N 5/00* | (2006.01) |
| *A61L 2/08* | (2006.01) |

(Continued)

(52) U.S. Cl.
CPC . *A61L 2/087* (2013.01); *B67B 1/03* (2013.01); *B67B 3/003* (2013.01); *A61L 2202/23* (2013.01)

(58) Field of Classification Search
CPC ............... A61L 2/00; A61L 9/03; A61L 9/18; A61L 9/20
USPC ................ 422/1, 22, 24, 186.04; 250/455.11, 250/492.1, 492.3
See application file for complete search history.

(56) References Cited

U.S. PATENT DOCUMENTS

| | | | |
|---|---|---|---|
| 4,944,132 A | 7/1990 | Carlsson et al. | |
| 7,832,185 B2 * | 11/2010 | Mastio et al. | ........... 53/426 |

(Continued)

FOREIGN PATENT DOCUMENTS

| | | |
|---|---|---|
| DE | 3808058 | 9/1989 |
| DE | 102010012569 | 9/2011 |

(Continued)

OTHER PUBLICATIONS

Search Report issued on Nov. 29, 2012 in corresponding German Application No. 10 2012 103 116.9.

(Continued)

*Primary Examiner* — Monzer R Chorbaji
(74) *Attorney, Agent, or Firm* — Onello, & Mello, LLP.

(57) ABSTRACT

A closure sterilization arrangement for container closures comprises a conveying device that conveys the container closures separately along a conveying path so that they avoid touching one another. An irradiation device generates a radiation sterilizing the container closures and acts upon the container closures with the radiation during the conveying thereof by the conveying device. A rotating device rotates the container closures about a pre-set axis of rotation at least for a time period during their conveying by the conveying device. The irradiation device is arranged with respect to the conveying path of the container closures so that the radiation issuing from the irradiation device strikes both an external peripheral wall of the container closures and an internal region of the container closures, and the irradiation device irradiates the container closures from at least two different radiation directions.

20 Claims, 5 Drawing Sheets

(51) Int. Cl.
  *B67B 3/00*    (2006.01)
  *B67B 1/03*    (2006.01)

(56) References Cited

U.S. PATENT DOCUMENTS

| | | | |
|---|---|---|---|
| 8,132,598 B2 | 3/2012 | Mastio et al. | |
| 8,479,782 B2 * | 7/2013 | Mastio et al. | 141/89 |
| 8,511,045 B2 * | 8/2013 | Mastio et al. | 53/426 |
| 8,567,454 B2 | 10/2013 | Mastio et al. | |
| 8,834,808 B2 | 9/2014 | Drenguis | |
| 8,884,249 B2 | 11/2014 | Drenguis | |
| 2009/0013645 A1 | 1/2009 | Mastio et al. | |
| 2009/0013646 A1 | 1/2009 | Mastio et al. | |
| 2009/0013647 A1 | 1/2009 | Mastio et al. | |
| 2009/0013648 A1 | 1/2009 | Mastio et al. | |
| 2009/0017747 A1 | 1/2009 | Wu et al. | |
| 2009/0184262 A1 | 7/2009 | Bartel et al. | |
| 2009/0277135 A1 | 11/2009 | Mastio et al. | |
| 2011/0023420 A1 | 2/2011 | Mastio et al. | |
| 2012/0124941 A1 | 5/2012 | Mastio et al. | |
| 2012/0134878 A1 | 5/2012 | Silvestri | |
| 2013/0052089 A1 | 2/2013 | Drenguis | |
| 2013/0193344 A1 | 8/2013 | Drenguis | |

FOREIGN PATENT DOCUMENTS

| | | | | |
|---|---|---|---|---|
| JP | 2011171624 | | 6/2001 | |
| JP | 2002128030 | | 5/2002 | |
| JP | 2007076730 | | 3/2007 | |
| JP | 2008195428 | | 8/2008 | |
| JP | 2011213417 | | 10/2011 | |
| WO | 2009009681 | | 1/2009 | |
| WO | WO 2009009681 (A1) | * | 1/2009 | A61L 2/08 |
| WO | 2010013262 | | 2/2010 | |
| WO | WO 2010/013262 | * | 2/2010 | A61L 2/08 |
| WO | 2010128532 | | 11/2010 | |
| WO | 2012000573 | | 1/2012 | |
| WO | 2012069101 | | 5/2012 | |

OTHER PUBLICATIONS

German Search Report dated Aug. 22, 2013, issued in European Application No. 13163129.3.

* cited by examiner

Fig. 1
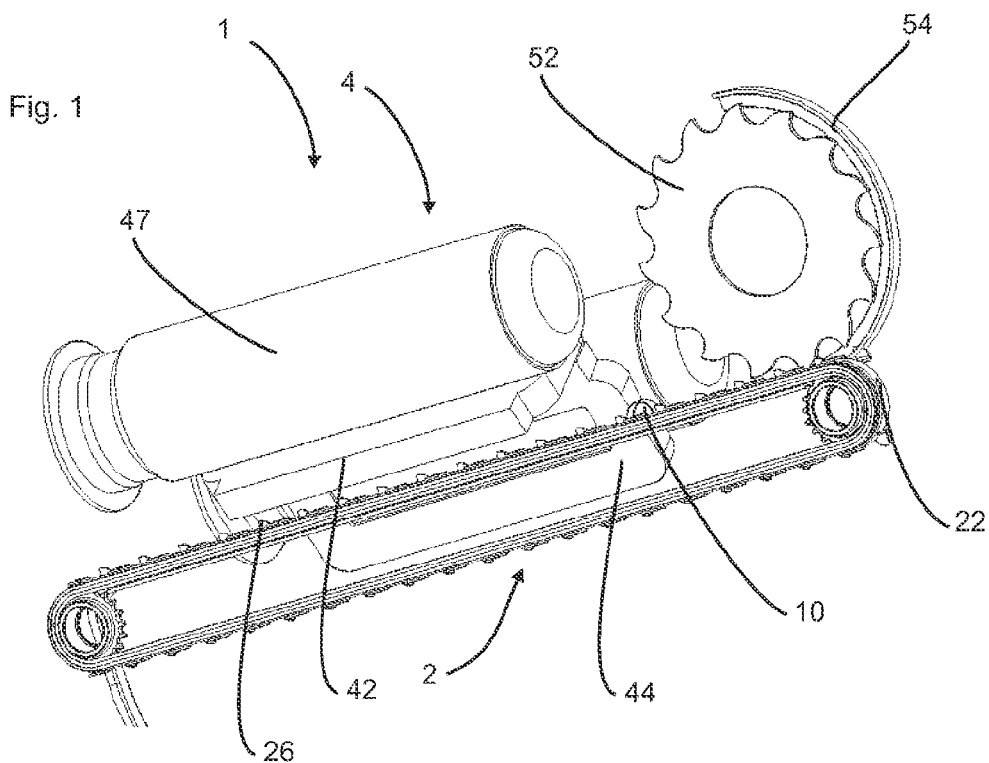
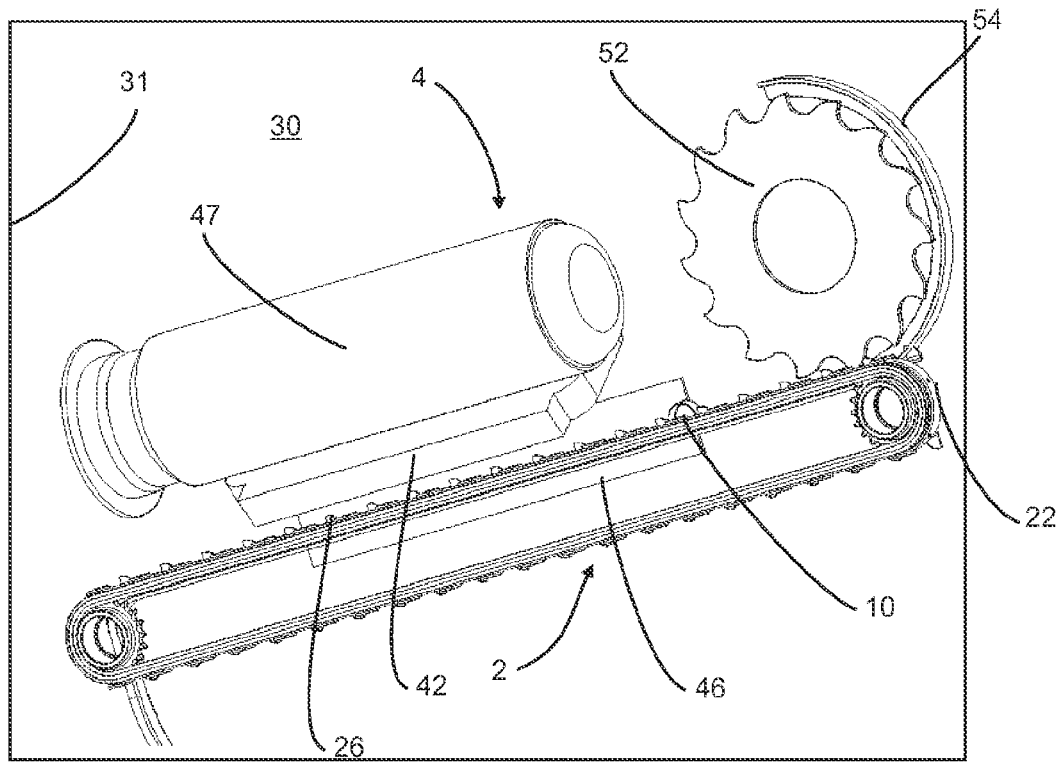
Fig. 2

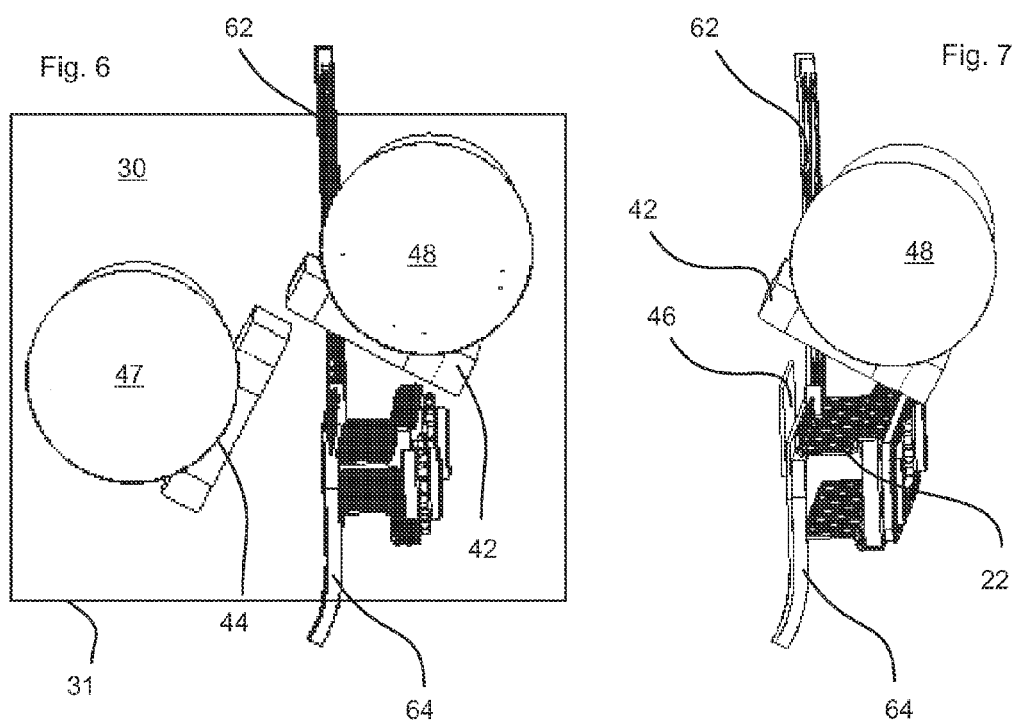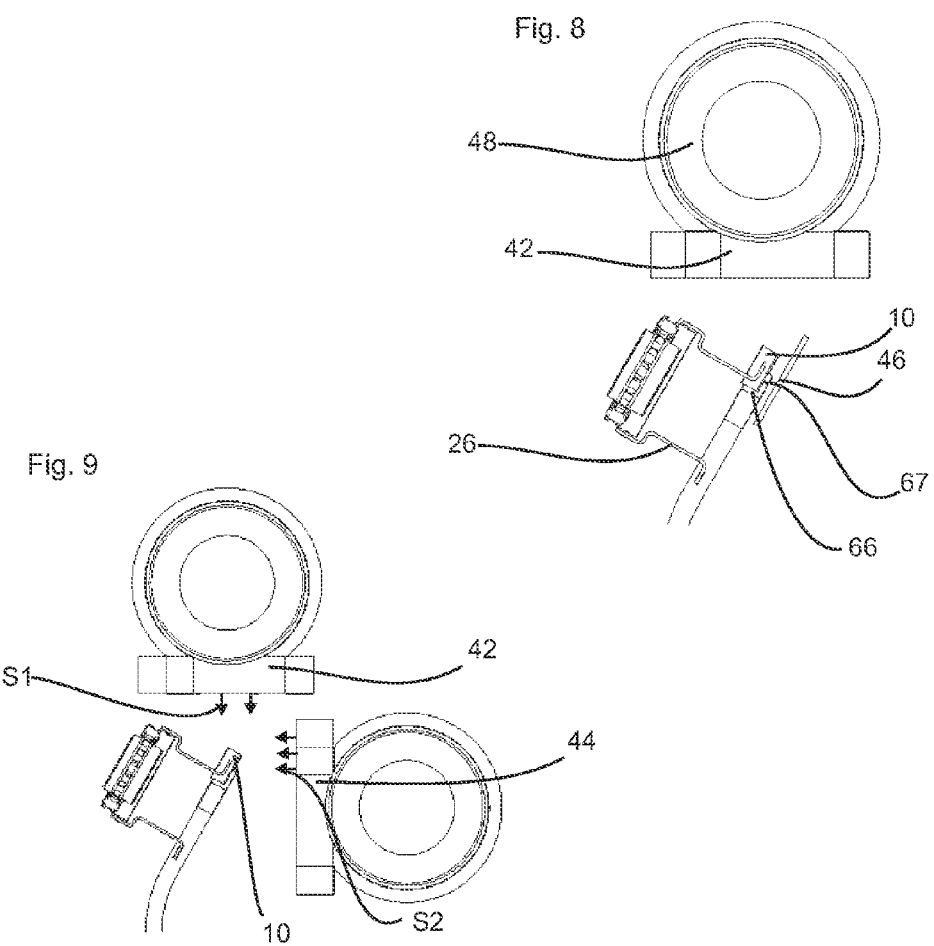

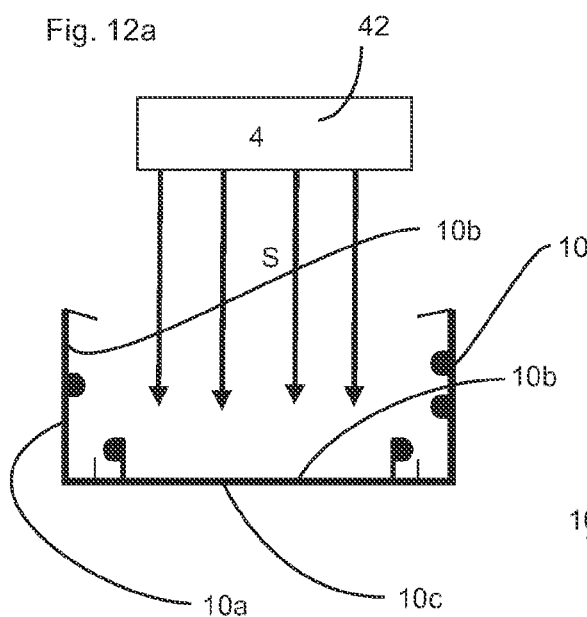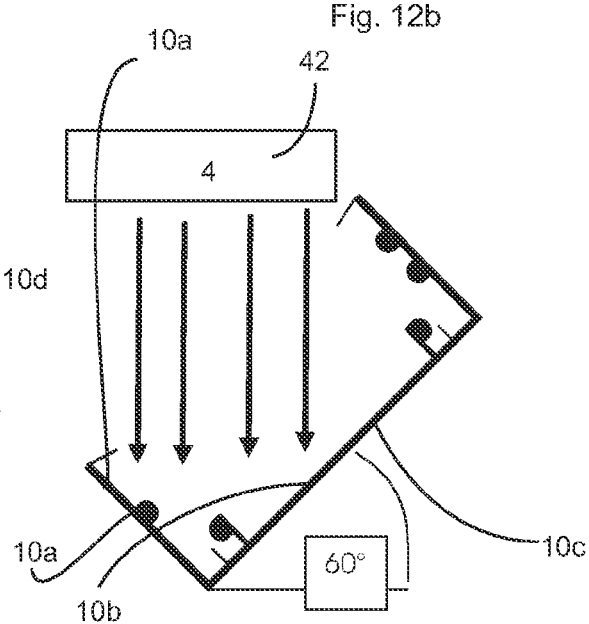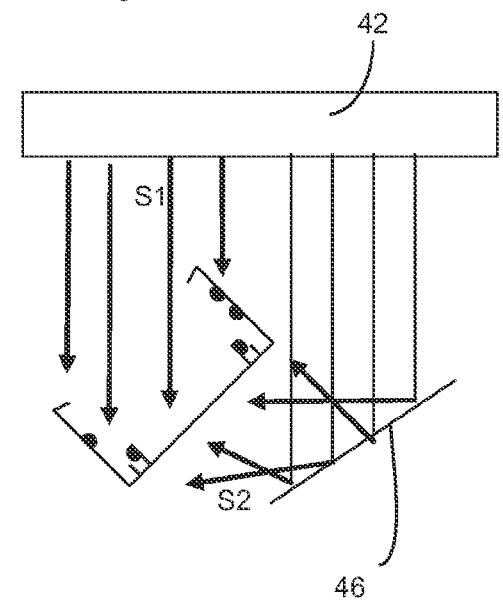

APPARATUS AND METHOD OF RADIATION-BASED STERILIZATION OF CONTAINER CLOSURES

RELATED APPLICATIONS

This application claims priority to German patent application number 10 2012 103 166.9 filed Apr. 11, 2012, the entire content of which is incorporated herein by reference, in its entirety.

DESCRIPTION

Embodiments of the present inventive concepts relate to an apparatus and a method of radiation-based sterilization of container closures. Various methods of sterilizing container closures are conventionally known. In this case it is known on the one hand to sterilize the container closures by means of a chemical medium, such as for example hydrogen peroxide. More recently, however, it has been necessary in part to dispense with the use of chemicals in this way.

Conventional apparatus and methods are therefore also known which sterilize the container closures by means of radiation. Radiation is understood herein as being in particular a radiation of charge carriers, i.e. for example a stressing with electrons. In addition, however, the radiation can also take the form of a different type of radiation, such as for example ultraviolet radiation, radioactive radiation, X-ray radiation and the like.

A unit and a method of sterilizing container closures are known from WO 2010/128 532 A1. In this case the container closures are guided in a rolling manner along a conveying path and are irradiated with electron radiation during the rolling movement.

The two electron radiation units in this case are arranged opposite with respect to the container closures to be sterilized. This apparatus thus allows an inner base area of the closures and also the outer surface opposite the latter to be sterilized. In this way, this inner face can be sterilized here, irrespective of the orientation in which the closure rolls through the apparatus. This apparatus nevertheless does not allow an adequate sterilization of the external peripheral regions of the container closures.

JP 2007 0 767 730 likewise discloses a sterilization apparatus for the sterilization of container closures by means of electron radiation. In this case, too, the container closures are conveyed along a pre-set path, so that they pass through the radiation. With this apparatus it is possible for the container closures to be rotated and to be irradiated by the electron irradiation device.

JP 2002 1 280 30 A likewise describes an apparatus for the sterilization of closures. With this apparatus the container closures are conveyed between two conveyor belts which can move at different speeds, so that the container closures are rotated. In the case of this apparatus, too, a sterilization of the peripheral surface of the container closures is possible only with difficulty.

SUMMARY

Embodiments of the present inventive concepts therefore provide an apparatus and a method of sterilizing container closures, which permits both a sterilization of the peripheral wall of the closures and a sterilization of the inner surfaces of these container closures. The inner surfaces are to be understood herein as being those regions of the closures which, in particular, are screwed onto the aperture of containers.

A closure sterilization arrangement according to the inventive concepts for container closures includes a conveying device which conveys the container closures separately along a pre-set conveying path. In this case this conveying device includes a drive device for driving the conveying device. In addition, the apparatus includes an irradiation device which generates a radiation sterilizing the container closures and which acts upon the container closures with this radiation during the conveying thereof by the conveying device. In addition, the apparatus includes a clean room, inside which the container closures are conveyed at least for a time during the sterilization thereof.

According to the inventive concepts the closure sterilization means has a rotating device which rotates the container closures about a pre-set axis of rotation at least for a time during their conveying by the conveying device, the irradiation device being arranged with respect to the conveying path of the container closures in such a way that the radiation issuing from the irradiation device strikes both an external peripheral wall of the container closures and an internal region of the container closures.

According to the inventive concepts the irradiation device additionally irradiates the container closures from two different directions. Although a precise physical radiation direction is not indicated, in particular in the case of the irradiation of objects with charge carriers such as in particular electrons, the irradiation direction is nevertheless to be understood in particular as being that direction in which the charge carriers on average strike the container to be sterilized. In some embodiments, this can be a direction which is substantially at a right angle to an outlet window of a charge carrier generation device. In addition, the radiation direction can be a geometrical direction which extends from the radiation device to the container closures.

For this purpose the irradiation device can include a plurality of radiation means or radiation devices which are arranged in such a way that the container closures can be irradiated simultaneously from a multiplicity of directions. In this case an angle between these two directions, in various embodiments, can be greater than 30°, greater than 45°, greater than 60° and greater than 80°. On the other hand the aforesaid angle between the directions can be smaller than 180°, smaller than 150°, particularly smaller than 120° and particularly smaller than 100°. The angle between these two directions can be defined in this case in a plane which is at a right angle to the conveying path of the container closures. It is thus advantageous for the two directions also not to be opposed to each other. This irradiation can ensure that—in particular in conjunction with the rotation of the container closures described above, also referred to only in brief as closures hereinafter—essentially all the regions of the container closures are acted upon with the aforesaid irradiation.

It is therefore proposed according to the inventive concepts that the irradiation can be arranged in such a way that both the internal region of the container closures is sterilized and the external peripheral wall and, particularly, also an external base area.

It is advantageous for the irradiation device to be an electron radiation means, i.e. the irradiation device has a generation device for electrons as well as advantageously also an acceleration device which accelerates the electrons in the direction of the container closures. In this case this acceleration device can accelerate the charge carriers, in particular electrons, for example to energy levels in the range of from 100 to 200 keV.

In the case of a further advantageous embodiment the irradiation device includes a first irradiation device, which directs radiation onto the container closures in a first pre-set direction, and a second radiation device, which directs radiation onto the container closures in a second pre-set direction which is different from the first direction. For this design two radiation devices which are capable of being controlled independently of each other are therefore provided.

In particular, the directions of the geometrical connecting lines between the respective radiation devices and the closures are different in this case.

In the case of a further advantageous embodiment the irradiation device includes a first radiation device, which directs radiation onto the container closures in a first pre-set direction, and a radiation re-direction device, which re-directs part of the radiation issuing from the first radiation device onto the container closures, in particular in such a way that the two radiations strike the container closures in the different directions. In this case reflector sheets of an atomically dense material, such as for example gold (or with a gold coating respectively) are possible as radiation devices of this type.

The active conveying device mentioned above is therefore understood as meaning that the container closures move not only along a conveying channel for example but are also driven in an active manner. In the case of further methods known from conventional approaches, during the irradiation the container closures are present in a closure channel which on the basis of its configuration both pre-sets the conveying direction of the closures and provides for the advance on the basis of the inclination thereof. Channels of this type are frequently made open in this case, so that as much radiation as possible strikes the closure.

Nevertheless, shadowing effects cannot be prevented in this case, since the closure neither rolls in a controlled manner nor is moved in an active manner. Although the channel can be opened on one side in short channel portions, for the secure guidance of the closure it is necessary for at least three quarters of the contour of the closures to be surrounded. In the conventional approach the separation of the closures is carried out for example with a star wheel, so that each closure slides individually into the chamber. The speed can be monitored and results from the time difference between the entry and the exit. An active influencing of the speed, however, is not possible.

In addition, it is difficult in the conventional approach to overcome breakdowns which can occur on account of defective closures which become caught. The treatment chamber is comprehensively screened off on account of the X-ray radiation produced. A rapid engagement to overcome the breakdown is frequently not possible in this case. In addition, a separating-out apparatus which can be advantageous for example for separating out defective closures is also not usually provided in the prior art. These drawbacks are at least largely overcome by the use of active conveying systems and also active separating and conveying and moving systems of the container closures inside the treatment chamber.

In the case of a further advantageous embodiment apparatus include a separating device which ensures that the container closures arrive separately in the conveying device, i.e. in such a way that the container closures do not touch one another during the conveying of the latter.

The above-mentioned rotation device, which rotates the container closures about a pre-set axis of rotation at least for a time during their conveying by the conveying device, can likewise have a different configuration. In this way, it would be possible for example for the container closures to be conveyed along a conveying path by means of individual entrainment means, in which case it is advantageous for these entrainment means to be arranged on a conveying means, which in some embodiments is a linear conveying means, such as a belt or a chain. In this case it is possible for the container closures to be spaced by way of a one-stroke star wheel and transferred individually to these entrainment means.

It is advantageous in this case for the container closures to be displaced on a horizontal path or "on end" respectively.

In the case of a further advantageous embodiment the conveying device is therefore designed in such a way that it conveys the container closures at least for a time during the sterilization thereof, in such a way that an axis of symmetry of the container closures is orientated obliquely with respect to an irradiation direction of the sterilizing radiation. In this case it is both possible for the container closures per se to be conveyed obliquely with respect to a horizontal plane and it would also, however, be possible for the container closures themselves to be conveyed in a horizontal or vertical plane and for the radiation device to irradiate the radiation obliquely with respect to these planes.

As a result of this oblique setting it is possible, in particular with a rotational movement of the container closures, for all the inner and outer regions of the closures to be sterilized or irradiated by the irradiation device.

In the case of a further advantageous embodiment the conveying device has support members which support the container closures at least in part on the base areas thereof during their conveying. In this way, it is possible for example for the container closures to be supported on a region of the peripheral wall thereof on one side and on the base areas thereof on the other side and then to be moved by the entrainment means.

In the case of a further advantageous embodiment the conveying device has a first contacting device which contacts the container closures during the conveying thereof on a region of their outer wall, and in some embodiments their peripheral wall. In addition, it is advantageous for the conveying device to have a second contacting device which contacts the container closures during the conveying thereof on a region of their outer wall, in some embodiments their peripheral wall or an outer base area. It would also be possible for the two contacting devices to contact the container closures on the outer base areas thereof and for a rotation of the container closures to be carried out for example by a relative speed between these contacting devices.

It is advantageous for the closures to be contacted by the rotation device or contact elements of this rotation device on two faces and, in particular, on two faces or areas (it being possible for these areas also to be virtually or substantially lines) which are arranged at a distance from each other and which are arranged at an angle different from 0° or 180° to each other. It is advantageous for the aforesaid faces or areas to be substantially at a right angle to each other. In this way, it is possible for an outer wall of the container closures and a base area to be contacted, or even two areas of the outer wall which are arranged substantially at a right angle to each other. It is advantageous, however, for the contacting areas to be outer wall areas of the container closures, i.e. in particular those areas which do not come into contact with the container to be closed.

If two regions of the peripheral wall of the container closure are contacted, tangents to the peripheral wall in these regions can, in various embodiments, be at an angle of between 30° and 150°, between 60° and 120°, between 80° and 100° and at an angle of approximately 90° with respect to each other.

In this case it is advantageous for a coefficient of friction between the first contacting device and the outer surface or peripheral wall of the container closures to be different from a coefficient of friction between the second contacting device and the outer surface or peripheral wall of the container closures. In this way, a controlled rotation of the container closures about the pre-set axis of rotation can occur. It is advantageous for this axis of rotation to extend at a right angle to the base area of the container closures and, in some embodiments, also parallel to the aforesaid peripheral walls.

It is thus possible for example for a support area, i.e. the first contacting device, to have a serrated surface, which for example corresponds to the negative shape of the fluting of the outside of the closure. In this way, the closure interlocks with the support area and has to roll away in a defined manner.

As a result of the above-mentioned oblique setting of the container closures and the tendency thereof to tilt toward the rear, it is also possible to dispense with a guidance on the open front side and, in this way, radiation can arrive in particular in the inside of the closures without obstruction. In addition, it is possible to vary the above-mentioned oblique setting of the container closures or the angle of inclination thereof and thus to achieve different angles of irradiation. In the case of this embodiment the container closures are therefore not only rotated about the aforesaid axis of rotation, but the inclination thereof along the conveying path is likewise altered.

In this way, the above-mentioned radiation directions of the irradiation directed onto the container closures is thus also changed along the conveying path. By way of example, a vertical irradiation can thus serve to reach the depths of the sealing lips of the container closures, and an oblique irradiation to be able to reach the areas of the thread better. In addition, it can also be provided that the container closures are rotated only along the portion of the conveying path thereof with respect to the above-mentioned axis of rotation and are merely conveyed in other areas.

It is thus advantageous for the apparatus to have an inclination altering device which alters an inclination of the container closures with respect to the conveying path thereof.

As mentioned above, it is possible for two emitters or radiation devices to be provided, one being used for the inside of the closures and one for the outside of the closures. In this case, in contrast to known systems, these radiation devices are advantageously arranged not opposite each other but at an angle, which differs from this and which is advantageously between 30° and 150°, advantageously between 60° and 120°, advantageously between 75° and 105° and in one embodiment, approximately 90°, with respect to each other.

The above-mentioned radiation re-direction device can comprise for example a scattering plate or a reflector which has the effect that the radiation—passing close to the closure—from the emitter of the internal treatment is scattered and reflected in such a way that the rear side of the closure can thus be sterilized.

In addition, it is also possible for the sterilization device to have a detection device for so-called radiation breakdowns. In particular, in the case of irradiations of electrons, it can happen that as a result of so-called arcs the electron radiation breaks down for a short time. In this case the sterilization is also prevented. Here it is possible for a control device to control the conveying device in such a way that the conveying of the container closures is stopped when breakdowns of this type occur. In this way, it is possible to prevent container closures from remaining untreated or from being treated for less long than intended. In addition, if there were a threat of an over-treatment of the container closures during the restarting of the radiation device, it is also possible for the conveying device to convey the container closures in a direction contrary to the conveying path, i.e. towards the rear, in order for example to empty the container closures out of the conveying device.

In the case of a further advantageous embodiment the apparatus has an ejection device by which individual container closures can be separated out from the conveying path. In this way, for example, defective container closures can be separated out, or even container closures which have been acted upon with a radiation dose which was too low or too high.

The above-mentioned second contacting device can be for example a movable slide or entrainment means and the first contacting device can be for example a stationary plate. It is thus advantageous for one of the two contacting devices to be arranged so as to be stationary and, in some embodiments, for the other to be arranged so as to be movable. As a result, the treatment speed for the container closures can be influenced or altered by a control means for the drive device.

It is also possible, however, for the container closures to be conveyed at least for a time by means of two conveyor belts which move at a different speed.

The present inventive concepts further relate to a method of sterilizing container closures, in which the container closures are conveyed along a pre-set conveying path by means of a conveying device in such a way that they do not mutually touch one another at least for a time during this conveying. In this case the container closures are irradiated with a sterilizing irradiation by means of at least one irradiation device at least for a time during this conveying.

According to the inventive concepts the container closures are rotated about a pre-set axis of rotation at least for a time during the sterilization thereof and in this case both a peripheral wall, in particular an outer peripheral wall of the container closures, and an internal region of the container closures [are] irradiated by the irradiation device.

In particular, the container closures are irradiated with charge carriers, i.e. in more precise terms are acted upon with the charge carriers. These charge carriers are, in particular, electrons.

In the case of a further advantageous method a base area of the container closures is also irradiated at least for a time.

It is advantageous for the container closures to be conveyed through a clean room at least for a time during their sterilization. In this case this clean room can be acted upon for example with sterile air and it is advantageously separated from the surroundings. It is particularly advantageous for the clean room to be acted upon with a sterile inert gas such as for example nitrogen or helium, in order to keep the interactions of the electrons with the gas molecules as low as possible in this way.

It is advantageous for the container closures to be irradiated from at least two different radiation directions. It is advantageous for the container closures to be plastics material closures. These are suitable in a particular way for being acted upon with charge carriers.

In the case of a further advantageous method the container closures are separated in particular before the sterilization.

The present inventive concepts further relate to a container treatment plant with a closure sterilization arrangement of the type specified above. In the conveying direction of the closures downstream of the closure sterilization arrangement this plant has a closure device which closes containers with the closures. It is advantageous in this case for this closure device also to be arranged inside a clean room.

In some embodiments, the container treatment plant can also include a sterilization device for the sterilization of the containers to be closed, it being advantageous for this sterilization device to act upon at least one wall of the containers and in some embodiments at least one inner wall of the containers with radiation and, in particular, with electron radiation.

In some embodiments, a closure sterilization arrangement for container closures comprises: a conveying device that conveys the container closures separately along a conveying path so that they avoid touching one another; an irradiation device that generates a radiation sterilizing the container closures and that acts upon the container closures with the radiation during the conveying thereof by the conveying device; a rotating device that rotates the container closures about a pre-set axis of rotation at least for a time period during their conveying by the conveying device, wherein the irradiation device is arranged with respect to the conveying path of the container closures so that the radiation issuing from the irradiation device strikes both an external peripheral wall of the container closures and an internal region of the container closures, and wherein the irradiation device irradiates the container closures from at least two different radiation directions.

In some embodiments, the irradiation device comprises: a first irradiation device, which directs radiation onto the container closures in a first pre-set direction; and a second radiation device, which directs radiation onto the container closures in a second pre-set direction which is different than the first direction.

In some embodiments, the irradiation device comprises: a first radiation device, which directs radiation onto the container closures in a first pre-set direction; and a radiation re-directing device, which re-directs part of the radiation issuing from the first radiation device onto the container closures.

In some embodiments, the conveying device is constructed and arranged to convey the container closures at least for a time period during the sterilization thereof, so that an axis of symmetry of the container closures is orientated obliquely with respect to an irradiation direction of the sterilizing radiation.

In some embodiments, the conveying device comprises support members that support the container closures at least in part on the base areas thereof during their conveying.

In some embodiments, the conveying device comprises a first contacting device which contacts the container closures during the conveying thereof at a region of their outer wall.

In some embodiments, the first contacting device contacts a peripheral wall of the container closures.

In some embodiments, the conveying device comprises a second contacting device which contacts the container closures during the conveying thereof at a region of their outer wall.

In some embodiments, the second contacting device contacts a peripheral wall of the container closures.

In some embodiments, a coefficient of friction between the first contacting device and the outer wall of the container closures is different than a coefficient of friction between the second contacting device and the outer wall of the container closures.

In some embodiments, the closure sterilization arrangement further comprises a drive device that drives the conveying device.

In some embodiments, the closure sterilization arrangement further comprises a clean room inside which the container closures are conveyed at least for a time period during the sterilization thereof.

In some embodiments, a method of sterilizing container closures comprises: conveying container closures along a pre-set conveying path by means of a conveying device in such a way that the container closures avoid touching one another for at least a time period during the conveying; irradiating the container closures with a sterilizing irradiation by means of at least one irradiation device for at least a time period during the conveying; and rotating the container closures about a pre-set axis of rotation for at least a time period during the irradiating thereof so that both a peripheral wall of the container closures and an internal region of the container closures are irradiated by the at least one irradiation device.

In some embodiments, a base area of the container closures is also irradiated for at least a time period during the conveying.

In some embodiments, irradiating comprises irradiating the container closures from at least two different radiation directions.

In some embodiments, the at least one irradiation device comprises: a first irradiation device, which directs radiation onto the container closures in a first pre-set direction; and a second radiation device, which directs radiation onto the container closures in a second pre-set direction which is different than the first direction.

In some embodiments, the irradiation device comprises: a first radiation device, which directs radiation onto the container closures in a first pre-set direction; and a radiation re-directing device, which re-directs part of the radiation issuing from the first radiation device onto the container closures.

In some embodiments, conveying comprises conveying the container closures at least for a time period during the irradiating thereof, so that an axis of symmetry of the container closures is orientated obliquely with respect to an irradiation direction of the sterilizing radiation.

In some embodiments, the conveying device comprises support members that support the container closures at least in part on the base areas thereof during their conveying.

In some embodiments, irradiating further comprises irradiating the container closures within a clean room for at least a time period of the irradiating thereof.

BRIEF DESCRIPTION OF THE DRAWINGS

Further advantages and embodiments are evident from the accompanying figures. In the drawings FIG. 1 is a partial illustration of an apparatus according to the inventive concepts;

FIG. 2 is a partial illustration of an apparatus according to the inventive concepts in a further embodiment;

FIG. 6 is a view of an apparatus according to the inventive concepts along the conveying path of the closures;

FIG. 7 is a view of a further embodiment of an apparatus according to the inventive concepts;

FIG. 8 is a further view of an apparatus according to the inventive concepts;

FIG. 9 is a further view of an apparatus according to the inventive concepts;

FIGS. 12a-12c are three diagrammatic illustrations to explain the inventive concepts.

DETAILED DESCRIPTION OF EMBODIMENTS

Figure 3:
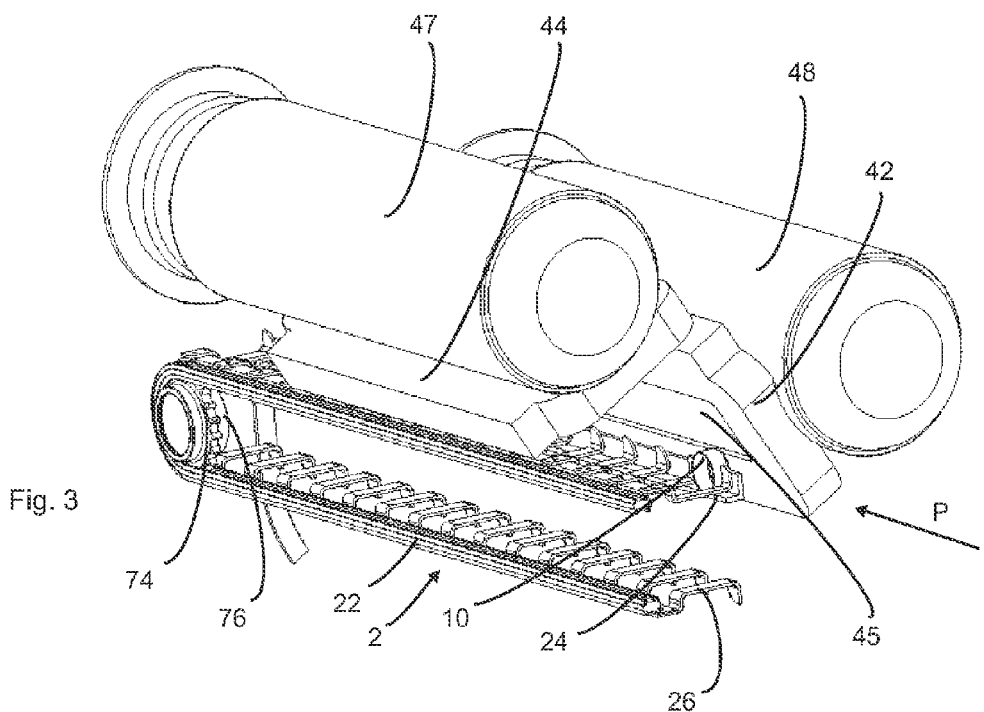
FIG. 3 is a partial illustration of an apparatus according to the inventive concepts in a further embodiment.

Exemplary embodiments in accordance with principles of inventive concepts will now be described more fully with reference to the accompanying drawings, in which exemplary embodiments are shown. Exemplary embodiments in accordance with principles of inventive concepts may, however, be embodied in many different forms and should not be construed as being limited to the embodiments set forth herein; rather, these embodiments are provided so that this disclosure will be thorough and complete, and will fully convey the concept of exemplary embodiments to those of ordinary skill in the art. Like reference numerals in the drawings denote like elements, and thus their description may not be repeated.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of exemplary embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of exemplary embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Exemplary embodiments in accordance with principles of inventive concepts are described herein with reference to cross-sectional illustrations that are schematic illustrations of idealized embodiments (and intermediate structures) of exemplary embodiments. As such, variations from the shapes of the illustrations as a result, for example, of manufacturing techniques and/or tolerances, are to be expected. Thus, exemplary embodiments in accordance with principles of inventive concepts should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of exemplary embodiments.

Unless otherwise defined, all terms (including technical and scientific terms) used herein have the same meaning as commonly understood by one of ordinary skill in the art to which exemplary embodiments in accordance with principles of inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 shows an apparatus 1 according to the inventive concepts in a first embodiment. In this case a conveying device designated 2 as a whole is provided, which conveys container closures 10. In this embodiment the container closures 10 are moved substantially on end in this case on a horizontal belt. The reference number 52 designates a single-stroke wheel which allows a separate supply of the container closures to the conveying device 2. In this case the container closures 10 are moved with respect to a rail 54 arranged in a stationary manner.

The reference number 22 refers to a conveyor belt which circulates here and on which a plurality of second contacting devices 26 are arranged in a fixed manner here. In this way, the second contacting devices move jointly with the conveyor belt 22 and therefore also in part in the direction of the conveying path of the container closures 10.

The reference number 42 refers to a first irradiation device which irradiates the container closures with electrons. The reference number 44 designates a corresponding second irradiation device which irradiates the container closures. The reference number 47 designates an electron generation device which generates the electrons which are used for the irradiation of the container closures 10. In this way, in this embodiment the container closures are irradiated with electrons from two directions, namely by the first radiation device 42 and by the second radiation device 44. These two radiation devices together form the irradiation device 4 for the irradiation of the container closures.

The irradiation device advantageously also can include a charge carrier generation device as well as a charge carrier acceleration device which accelerates the charge carriers which are generated in this way and which, in particular, are electrons.

FIG. 2 shows an apparatus according to the inventive concepts in a further embodiment. In this case the single-stroke wheel 52 mentioned above is again provided. The essential difference here is that in this case only one radiation device 42 is provided, but, in addition, a reflector element or a radiation re-direction device 46 is provided which reflects at least part of the radiation arriving from the first radiation device 42 and directs it onto the container closures 10 again. In this way, the container closures are irradiated from two directions in this embodiment as well.

It is advantageous in this case for the reflector element to direct the radiation onto an outer side or rear side of the container closures, which in terms of sterilization is less critical than the inner side of the closures, i.e. that side which comes directly into contact with the container to be closed.

The reference number 30 designates in a roughly diagrammatic manner a clean room, inside which the container closures are sterilized. This clean room can be bounded off in this case by a housing 31 from a (non-sterile) environment. In this case it would also be possible for this clean room 30 to be chosen to be smaller than shown in the figures and for it to surround the conveying device 2 in the manner of a channel for example, in which case it is advantageous for the radiation generation devices to be arranged outside the clean room and/or in some embodiments for the radiation devices 42 and 44 respectively to form part of the housing 31. It is advantageous, however, for this clean room also to extend in the direction of movement of the container closures 10 downstream with respect to the sterilization apparatus 1 and to be directly joined to a clean room in which a closure device for closing containers with the sterilized container closures is arranged. The container closures can be supplied to the clean room 30 for example by way of a separation device. It is advantageous for a sterile gaseous medium (for example sterile air) to be present inside the clean room 30, in particular at a pressure slightly higher than the ambient pressure.

FIG. 3 shows a further embodiment of an apparatus according to the inventive concepts. In this embodiment two radiation devices 42 and 44 are again provided, but, in addition, two separate or independent electron generation devices 47, 48 are also provided. The design of the conveying device 2 is also illustrated in greater detail in FIG. 3. The first contact devices 26, which contact the containers on the lateral edges thereof here, are in turn evident here. In addition, a second contacting device 24 of a rail, which is fixed or arranged in a stationary manner and with respect to which the container closures roll away, is provided.

In this case a coefficient of friction between the rail 24 and the container closures 10 is higher than a frictional resistance between the second contacting device 26 or the entrainment means 26 respectively and the container closures. In this way it is made possible for the container closures not only to be moved along the conveying path P but also to be rotated about an axis of rotation at a right angle to the lid face of the container closures. In this way a complete irradiation of the closures 10 is possible.

The reference number 74 refers to a driving gear wheel for driving a conveyor belt 22 and the reference number 76 to a drive device such as a motor. The reference number 45 designates an outlet window through which the electron radiation generated in the radiation generation device 48 can issue. This can be for example a titanium window. At this point it should be mentioned that, although electrons are involved in the radiation here, it would also be possible for a different type of radiation such as for example UV radiation or X-ray radiation or the like to be used as the radiation. The reference letter P designates the conveying path of the container closures.

Figure 4:
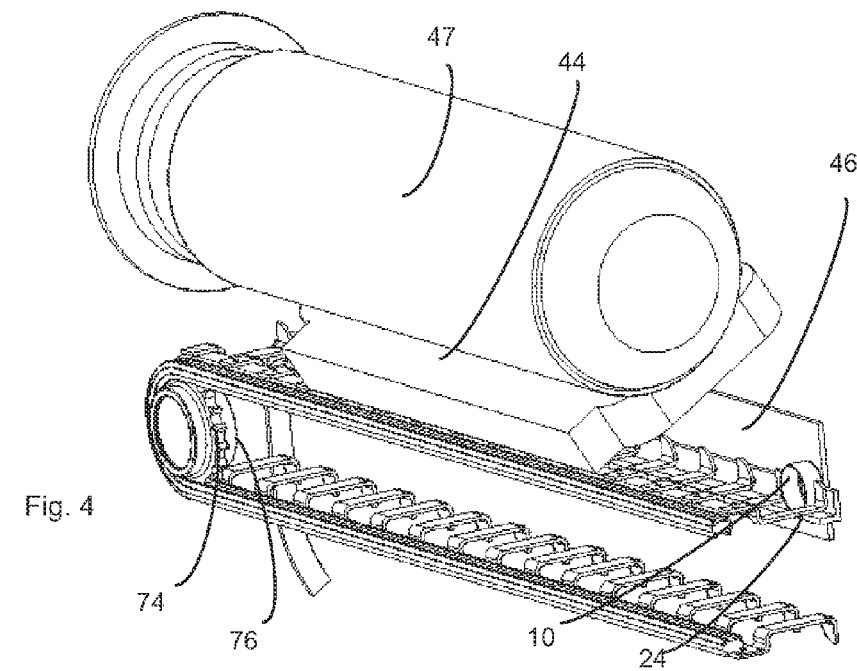
FIG. 4 is a further partial view of an apparatus according to the inventive concepts.

FIG. 4 shows a further embodiment of the apparatus according to the inventive concepts. In the case of this embodiment a second radiation device 42 is not provided, and therefore also the above-mentioned reflector element 46 which re-directs radiation issuing from the radiation device 44 onto the container closures.

Figure 5:
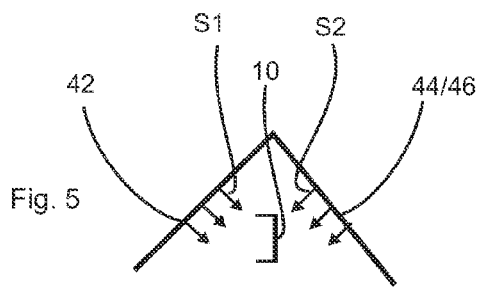
FIG. 5 is a diagrammatic illustration to explain the sterilization procedures.

FIG. 5 shows the irradiation of the container closures. It is evident that the container closures are acted upon with radiation in two directions (radiation direction S1 and radiation direction S2). In this case the two radiation directions S1 and S2 are substantially at a right angle to each other in this embodiment. In addition, as mentioned above, the container closure 10 is rotated, so that as a whole a complete irradiation of the container closures is possible during the conveying along the conveying path P.

FIG. 6 is a further illustration of an apparatus according to the inventive concepts. In this case too, two radiation devices 42 and 44 are provided. The container closures are supplied to the apparatus by way of a supply device 62, such as for example a supply channel, and the closures are removed again by way of a removal device which can likewise be a channel 64.

FIG. 7 shows a further design, in which case in this embodiment too only one radiation device 42 is provided, as well as a reflector element 46 which re-directs the radiation—in particular radiation which does not strike the closures directly—onto the container closures 10. In addition, the conveyor belt 22 is again evident here.

FIG. 8 is a diagrammatic illustration of the apparatus according to the inventive concepts. Whereas in FIG. 7 the radiation device 42 is set obliquely and the container closures are conveyed vertically, in the case of the embodiment shown in FIG. 8 the radiation device 42 is orientated horizontally, i.e. the radiation direction S1 extends first substantially in the vertical direction here. Part of the radiation is again redirected (S2) by way of the reflector element 46. The reference number 66 designates a holding device (arranged in a stationary manner) which in turn holds a conveying face 67, with respect to which the container closures slide. This conveying face 67 is provided in this case with a plurality of openings (not shown) through which the closures can be irradiated. In this way, in the case of the embodiment shown in FIG. 8 as well, a complete irradiation of the container closures 10 is possible.

In the case of the embodiment shown in FIG. 9, two radiation devices 42, 44 are again provided, which in this case irradiate the container closures at angles at a right angle to each other. It should be pointed out, however, that the radiation direction[s] S1 and S2 need not necessarily be at a right angle, but can also be at angles differing therefrom, for example between 60° and 120°.

Figure 10A:
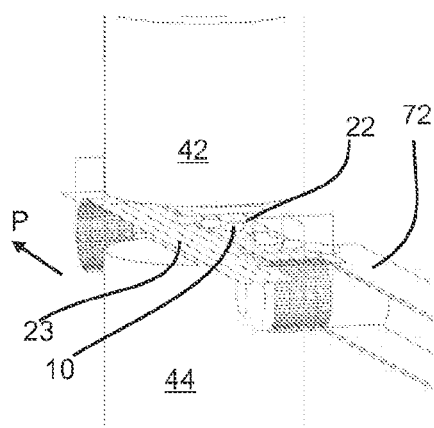
FIGS. 10a, 10b are two views of a further embodiment of an apparatus according to the inventive concepts.
Figure 10B:
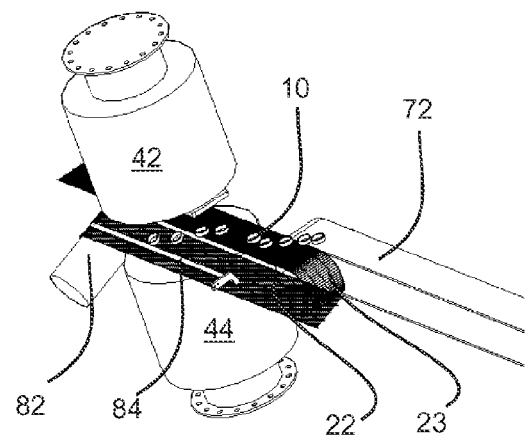

FIGS. 10*a* and 10*b* display a further design of an apparatus according to the inventive concepts. In the case of the embodiment shown in FIG. 10*a* a first conveyor belt 22 is again provided as well as a second conveyor belt 23 which conveys the container closures along the conveying path P. In this embodiment two radiation devices 42 and 44 are orientated in an opposed manner, in order to be able to irradiate the container closures 10 uniformly from all sides. The conveyor belt 22 and also the conveyor belt 23, on which on which the closures are conveyed at a slight distance from one another, extend horizontally in this case. In addition, the conveyor belt has a plurality of openings and is designed for example in the form of a wide-mesh conveyor belt, so that the closures can also be irradiated from below. On the top side the container closures 10 are not subjected to shadowing whatsoever, i.e. in this case the container closures 10 are in each case situated on the conveyor belts 22, 23 in such a way that their openings are directed upwards, i.e. in the direction of the radiation device 42.

In order also to minimize the shadowing on the rear side of the container closures, the conveyor belt or the conveyor chain respectively, as mentioned above, can be designed in the form of a chain with a high-grade steel mat with as large a screen width or mesh width as possible. In addition, it would also be possible for the container closures 10 to rotate during the conveying thereof, for example by the two conveyor belts 22 and 23 moving at a different speed from each other.

FIG. 10b shows a further embodiment in which the conveyor belt 22 is, in addition, inclined differently in this case from the conveyor belt 23. It is evident here that a drive device 82, such as for example a re-directing roller, which drives the conveyor belt 22, is inclined. In this way, the radiation strikes the individual container closures 10 obliquely in this case as well. The reference number 84 designates a conveying web which supports the container closures 10 so that they do not fall downwards. In addition, a rotation of the container closures can, be achieved by this web which in this case also acts like the contacting device described above, as will be explained below. In this way, a complete irradiation of the container closures is also possible.

It is advantageous for the angle of inclination of the second conveyor belt 22 with respect to the first conveyor belt 23 to be, in various embodiments, in a range of between 10° and 60°, between 10° and 40°, and between 10° and 30°. The reference number 72 refers to a supply belt.

Figure 11A:
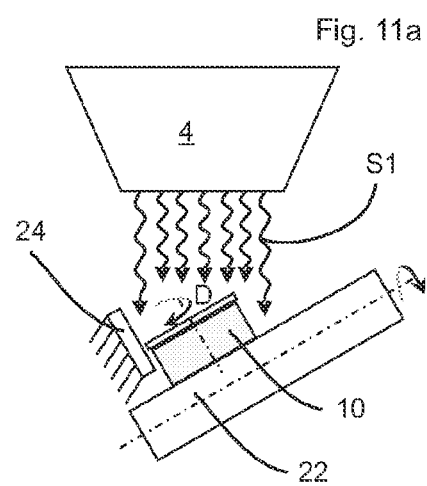
FIGS. 11a-11d are four diagrammatic illustrations to explain an apparatus according to the inventive concepts.

FIGS. 11a to 11d show different embodiments for achieving a rotation of the container closures 10. In the case of the embodiment which is shown in FIG. 11a and which is similar to the embodiment shown in FIG. 10b, a first contacting device 24 is provided which is arranged in a stationary manner in this case and with respect to which the container closures 10 roll away. In this case the container closures 10 are conveyed by means of the conveyor belt 22 and rotate, as shown, about their axis of rotation D.

Figure 11B:
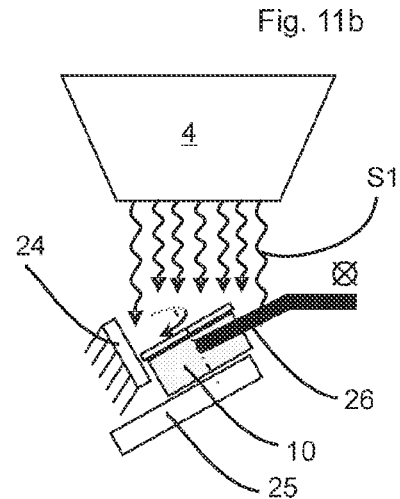

In the case of the embodiment shown in FIG. 11b, a support face 25—which can also be arranged in a stationary manner—is also provided for the container closures. In addition, second contacting devices 26 are provided which move the container closures 10 and thus also rotate them.

Figure 11C:
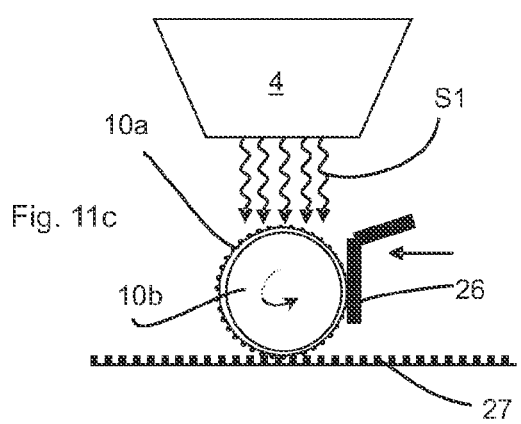

FIG. 11c shows a further embodiment for conveying the container closures. In this case an outer wall 10a of the container closures 10 is again illustrated as well as also an inner face or an inner region 10b. In this case the container closures 10 are moved on end on a horizontal path, i.e. a contact face has a fluting 27 which in this case mutually engages with a peripheral fluting of the container closure 10. In this case the container closure 10 meshes with the contact face and can thus roll away in a defined manner. As mentioned above, the container closure can, in addition, be set obliquely, in order to achieve radiation obliquely into the closure.

On account of the oblique setting of the closure, the tendency thereof to seek to tilt towards the rear can also be counteracted. In addition, it would also be possible for the container closures to be conveyed upwards slightly, so that it is possible to dispense with a guide from the front and the radiation can thus reach the inside of the closures without obstruction in this way. Furthermore, it would be possible for the angle of inclination of the closure to be varied during the conveying, for example from 60° to 0°, i.e. in a horizontal manner, in order to achieve different angles of irradiation in this way, for example a vertical irradiation in order to reach the deep portions of the sealing lips, as well as also an oblique setting in order to be able to reach the faces of the (internal) thread better.

Figure 11D:
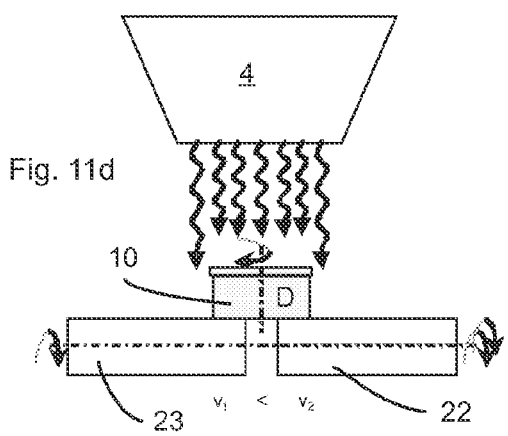

FIG. 11d shows a further embodiment which likewise causes a rotation of the container closures 10. In this case the closure 10 is moved on two conveyor belts 22, 23 which move at different speeds. In this way, a rotation of the container closure 10 about the axis of rotation D thereof also takes place.

In addition, it is also possible for a separation of the closures to be carried out by means of two belts running at different speeds. In this way, a slower supply belt can be provided as well as a forwarding belt running more rapidly, so that a distance between the container closures is increased.

On account of the procedure according to the inventive concepts a conveying of the container closures 10 independent of the form of closure is achieved. In contrast to the prior art, it is also possible for the speed to be controlled and monitored precisely. In addition, shade effects or shadowing effects respectively on the top side of the container closure can also be prevented completely and the shadowing effects on the underside can also be limited.

FIGS. 12a to 12c show once again diagrammatic illustrations in order to show the irradiation of the container closures 10. In this case the reference 10c refers to a lower outer base area of the container closure, the reference 10b refers to an inner base area of the closure, the reference 10a refers to an outer wall of the container closure 10 and the reference 10d refers to thread portions. In the case of the embodiment shown in FIG. 12a a vertical irradiation takes place, and in the case of the embodiment shown in FIG. 12b an irradiation at 60°. In the case of the embodiment shown in FIG. 12c two radiation directions are provided.

The Applicants reserve the right to claim all the features disclosed in the application documents as being essential to the inventive concepts, insofar as they are novel either individually or in combination as compared with the prior art.

What is claimed is:

1. A closure sterilization arrangement for container closures comprising:
    a conveying device that conveys the container closures separately along a conveying path so that they avoid touching one another, wherein the conveying device comprises a linear transport device;
    an irradiation device that generates a radiation sterilizing the container closures and that acts upon the container closures with the radiation during the conveying thereof by the conveying device;
    a rotating device that rotates the container closures about a pre-set axis of rotation at least for a time period during their conveying by the conveying device,
    wherein the irradiation device is arranged with respect to the conveying path of the container closures so that the radiation issuing from the irradiation device strikes both an external peripheral wall of the container closures and an internal region of the container closures, and wherein the irradiation device irradiates the container closures from at least two different radiation directions that are less than 180 degrees relative to each other.

2. A closure sterilization arrangement according to claim 1, wherein the irradiation device comprises:
    a first irradiation device, which directs radiation onto the container closures in a first pre-set direction; and
    a second radiation device, which directs radiation onto the container closures in a second pre-set direction which is less than 180 degrees relative to the first direction.

3. A closure sterilization arrangement according to claim 1, wherein the irradiation device comprises:
    a first radiation device, which directs radiation onto the container closures in a first pre-set direction; and
    a radiation re-directing device, which re-directs part of the radiation issuing from the first radiation device onto the container closures.

4. A closure sterilization arrangement according to claim 1, wherein the conveying device is constructed and arranged to convey the container closures at least for a time period during the sterilization thereof, so that an axis of symmetry of the container closures is orientated obliquely with respect to an irradiation direction of the sterilizing radiation.

5. A closure sterilization arrangement according to claim 1, wherein the conveying device comprises support members that support the container closures at least in part on the base areas thereof during their conveying.

6. A closure sterilization arrangement according to claim 1, wherein the conveying device comprises a first contacting device which contacts the container closures during the conveying thereof at a region of their outer wall.

7. A closure sterilization arrangement according to claim 6, wherein the first contacting device contacts a peripheral wall of the container closures.

8. A closure sterilization arrangement according to claim 6, wherein the conveying device comprises a second contacting device which contacts the container closures during the conveying thereof at a region of their outer wall.

9. A closure sterilization arrangement according to claim 8, wherein the second contacting device contacts a peripheral wall of the container closures.

10. A closure sterilization arrangement according to claim 8, wherein a coefficient of friction between the first contacting device and the outer wall of the container closures is different than a coefficient of friction between the second contacting device and the outer wall of the container closures.

11. A closure sterilization arrangement according to claim 1, further comprising a drive device that drives the conveying device.

12. A closure sterilization arrangement according to claim 1, further comprising a clean room inside which the container closures are conveyed at least for a time period during the sterilization thereof.

13. A method of sterilizing container closures, comprising:
conveying container closures along a pre-set conveying path by means of a conveying device in such a way that the container closures avoid touching one another for at least a time period during the conveying, wherein the conveying device comprises a linear transport device;
irradiating the container closures with a sterilizing irradiation by means of at least one irradiation device for at least a time period during the conveying, wherein irradiating comprises irradiating the container closures from at least two different radiation directions that are less than 180 degrees relative to each other; and
rotating the container closures about a pre-set axis of rotation for at least a time period during the irradiating thereof so that both a peripheral wall of the container closures and an internal region of the container closures are irradiated by the at least one irradiation device.

14. A method according to claim 13, wherein a base area of the container closures is also irradiated for at least a time period during the conveying.

15. A method according to claim 13, wherein the at least one irradiation device comprises:
a first irradiation device, which directs radiation onto the container closures in a first pre-set direction; and
a second radiation device, which directs radiation onto the container closures in a second pre-set direction which is different than the first direction.

16. A method according to claim 13, wherein the irradiation device comprises:
a first radiation device, which directs radiation onto the container closures in a first pre-set direction; and
a radiation re-directing device, which re-directs part of the radiation issuing from the first radiation device onto the container closures.

17. A method according to claim 13, wherein conveying comprises conveying the container closures at least for a time period during the irradiating thereof, so that an axis of symmetry of the container closures is orientated obliquely with respect to an irradiation direction of the sterilizing radiation.

18. A method according to claim 13, wherein the conveying device comprises support members that support the container closures at least in part on the base areas thereof during their conveying.

19. A method according to claim 13, wherein irradiating further comprises irradiating the container closures within a clean room for at least a time period of the irradiating thereof.

20. A closure sterilization arrangement for container closures comprising:
a conveying device that conveys the container closures separately along a conveying path so that they avoid touching one another, wherein the conveying device comprises a first contacting device which contacts the container closures during the conveying thereof at a region of their outer wall, wherein the conveying device comprises a second contacting device which contacts the container closures during the conveying thereof at a region of their outer wall, and wherein a coefficient of friction between the first contacting device and the outer wall of the container closures is different than a coefficient of friction between the second contacting device and the outer wall of the container closures;
an irradiation device that generates a radiation sterilizing the container closures and that acts upon the container closures with the radiation during the conveying thereof by the conveying device;
a rotating device that rotates the container closures about a pre-set axis of rotation at least for a time period during their conveying by the conveying device,
wherein the irradiation device is arranged with respect to the conveying path of the container closures so that the radiation issuing from the irradiation device strikes both an external peripheral wall of the container closures and an internal region of the container closures, and wherein the irradiation device irradiates the container closures from at least two different radiation directions that are less than 180 degrees relative to each other.

* * * * *